United States Patent [19]

Casellas et al.

[11] Patent Number: 4,749,566

[45] Date of Patent: Jun. 7, 1988

[54] PHARMACEUTICAL COMPOSITION COMPRISING A COMBINATION OF AT LEAST ONE IMMUNOTOXIN AND AT LEAST ONE MANNOSE-CONTAINING POLYMER

[75] Inventors: Pierre Casellas; Bernard Bourrie; Pierre Gros, all of Montpellier, France

[73] Assignee: Sanofi, France

[21] Appl. No.: 801,843

[22] Filed: Nov. 26, 1985

[30] Foreign Application Priority Data

Nov. 29, 1984 [FR] France ............................... 84 18203

[51] Int. Cl.[4] ............................................ A61K 39/395

[52] U.S. Cl. ....................................... 424/85; 530/391; 530/395; 530/403; 530/405; 514/2; 514/23; 514/54; 514/885; 435/810

[58] Field of Search .................. 424/85; 530/391, 395, 530/403, 405; 514/2, 23, 54, 885; 435/810

[56] References Cited

PUBLICATIONS

*Eur. J. Biochem.*, 155, 1986, pp. 1–10, Bourrie et al.

*EEBS*, vol. 196(2), 1986, pp. 344–348, Skilleter et al.

*Primary Examiner*—John Kight

*Assistant Examiner*—Garnette D. Draper

*Attorney, Agent, or Firm*—Bacon & Thomas

[57] ABSTRACT

The invention relates to pharmaceutical compositions comprising a combination of at least one immunotoxin and at least one mannose-containing polymer. This combination makes it possible to inhibit the rapid elimination of immunotoxins from the plasma after injection.

10 Claims, 3 Drawing Sheets

Figure 1:
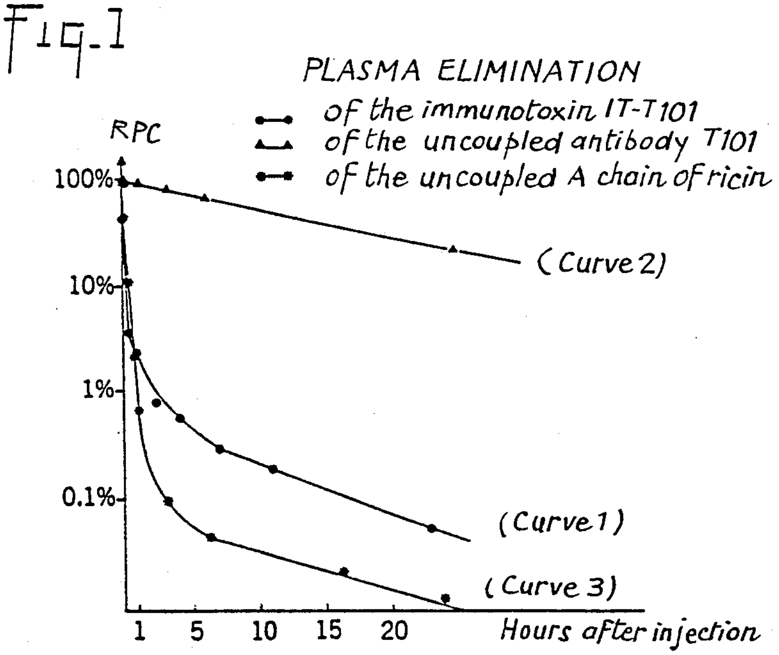
Figure 2:
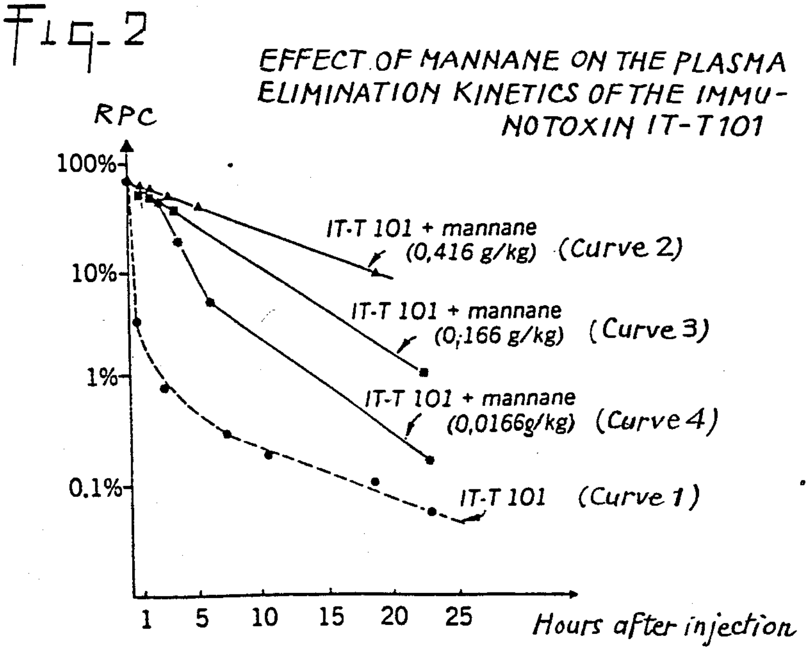

Fig.1 — PLASMA ELIMINATION
- of the immunotoxin IT-T101
- of the uncoupled antibody T101
- of the uncoupled A chain of ricin Fig.2 — EFFECT OF MANNANE ON THE PLASMA ELIMINATION KINETICS OF THE IMMUNOTOXIN IT-T101

HEPATIC FIXATION OF THE A CHAIN OF RICIN IN THE PRESENCE OR ABSENCE OF MANNANE

PHARMACEUTICAL COMPOSITION COMPRISING A COMBINATION OF AT LEAST ONE IMMUNOTOXIN AND AT LEAST ONE MANNOSE-CONTAINING POLYMER

In French Pat. No. 78/27838 and the patent for Addition attached thereto No. 79/24665 of the prior art, and in French patent Applications No. 81/07596 and No. 81/21836, the Applicant Company described the preparation of anticancer products, called conjugates, obtained by the coupling, by means of a covalent bond, of the A chain of ricin with antibodies or antibody fragments directed against an antigen carried by the cell to be destroyed. Products of this type are denoted in the present Application by the generic name of immunotoxins. The immunotoxin which is used in the present invention can be obtained from a natural, semisynthetic or synthetic toxin, toxic sub-unit or fragment of toxic subunit comprising polysaccharide groups containing mannose residues, in particular in the terminal position, irrespective of the constituent antibody and irrespective of the type of bond chosen to join the antibody of the toxin, toxic sub-unit or toxic fragment.

In its French Patent Applications No. 81/21836, No. 82/02091, No. 82/04119, No. 82/04047 and No. 82/04547, the Applicant Company also showed the ability of certain substances (ammonium salts, monovalent carboxylic ionophores, methylamine, chloroquine and enzyme conjugates capable of releasing ammonia) to potentiate the cytotoxic action of immunotoxins.

However, the therapeutic effects of activated or non-activated immunotoxins can only manifest themselves fully if the immunotoxin is capable, with its antibody part, of becoming localized in vivo, in the active form, on the target cell to be destroyed (a indispensable condition for all expression of activity by immunotoxins). The ability of the immunotoxin to become localized on the target depends first and foremost on the ability of the immunotoxin to remain in the bloodstream and the extracellular fluids, in the active form, for sufficient periods of time to reach its target cell and at sufficiently high concentrations to give a high degree of occupation of the corresponding antigen sites.

The Applicant Company has carried out a large number of studies which have made it possible to establish the plasma elimination kinetics of immunotoxins after intravenous injection into various animal models. It has been found that, after injection, the plasma level of biologically active immunotoxin decreases very rapidly and very substantially. Thus, in a typical case involving rabbits, in a model using an immunotoxin built up by coupling the A chain of ricin, by means of a link containing a disulfide bridge, with a monoclonal antibody directed against the antigen T65 of human T lymphocytes, it is found that 97% of the immunotoxin present in the bloodstream at time 0 after injection disappears in 30 minutes and 99.9% disappears in 17 hours. The results obtained are analogous if the link joining the antibody to the A chain of ricin contains a thioether bond instead of a disulfide bond. This rapid disappearance of the immunotoxin quite obviously detracts from the expression of its complete cytotoxic capacity, the immunotoxin being prevented from durably saturating a high proportion of the target antigens carried by the cells to be destroyed. Moreover, a comparison of the plasma elimination kinetics of immunotoxins with those of the corresponding unconjugated antibodies shows by contrast that—as is well known—the antibodies remain in the plasma at a high level for relatively long periods of time. Now, even in the most highly purified immunotoxin preparations, there is always a certain residual level of unconjugated antibodies. Due to the effect of the differential rates of elimination of immunotoxins and antibodies, the unconjugated antibodies, which are initially very much in the minority, gradually become the majority component after a few hours, so these antibodies gradually compete to become powerful antagonists for the fixation of the immunotoxins to their targets.

These studies clearly show the value of enhancing the persistence of immunotoxins in the plasma, in their active form, so as to increase both the duration and degree of occupation of the target antigens and consequently to improve the therapeutic effects of the immunotoxins.

The present invention relates to a pharmaceutical combination which makes it possible to inhibit the rapid elimination of immunotoxins from the plasma after injection, without adversely affecting the characteristic intrinsic properties of the immunotoxins. It has been found that the presence in the plasma of a combination of at least one immunotoxin and at least one mannose-containing polymer inhibits the rapid elimination of immunotoxins from the plasma after introduction of the immunotoxin in the plasma without adversely affecting the characteristic intrinsic properties of the immunotoxins.

Surprisingly, it has been found, according to the present invention, that mannanes constitute a particularly valuable type of substance for increasing the plasma levels of immunotoxins. The term mannane is used here to denote any polyoside or polysaccharide carbohydrate polymer which has an average molecular weight greater than 1000 and contains a large proportion of mannose residues, more particularly from 20 to 100% of mannose residues, irrespective of the type of osidic linkage joining these mannose residues to one another or to other sugars. In particular, and by way of a non-limiting example, it is possible within the terms of the present invention to use natural mannanes isolated from yeasts (for example Saccharomyces cerevisiae), i.e. the carbohydrate fraction of a peptidoglycan belonging to the cell wall of these yeasts. The protein-mannane complex is a mixture of macromolecules in which the polysaccharide component represents 50 to 90% of the complex. The mannane fraction is itself a polymer of D-mannose. It consists of a framework of mannose residues coupled in the $\alpha 1 \rightarrow 6$ position, with added side-chains of different lengths containing $\alpha 1 \rightarrow 3$ and $\alpha 1 \rightarrow 2$ bonds.

Surprisingly, mannane, used at doses in which it shows no toxicity to the animal, either on its own or in association with the immunotoxin, makes it possible to increase the plasma concentration of immunotoxins by an extremely large factor (of the order of 100) for prolonged periods; thereby considerably improving their localization on the target and avoiding fixation inhibition phenomena due to the presence of free antibodies in the preparations, as indicated previously.

The noteworthy absence of toxicity of mannanes makes them preferred substances for pharmaceutical use in association with immunotoxins. Association of the immunotoxin with the mannane does not significantly increase the inherent toxicity of the immunotoxin, nor does this association interfere with the specific cytotoxicity properties characteristic of the immunotoxins in the presence or absence of the potentiators already described.

Furthermore, experiments involving in vivo localization of the radiolabeled immunotoxin injected into animals with no specific target have shown that the conjugate becomes localized preferentially in the liver during the first few minutes after injection. The same applies to the A chain, which follows the same pattern when injected in the uncoupled form. This strongly suggests that the immunotoxin becomes fixed in the liver via the A chain of ricin contained in the immunotoxin. It is known that the A chain of ricin is a glycoprotein whose polyosidic groups comprise mannose residues and N-acetylglucosamine residues, the mannose residues being in the terminal position (Agri. Biol. Chem. (1978) 42, 501). Also, receptors capable of recognizing glycoproteins containing these terminal mannose residues have been found to exist in the liver.

It has thus been shown that the glycoproteins recognized by these receptors—the latter being present essentially on the Kupffer cells—are rapidly eliminated from the bloodstream by fixation to these cells, which metabolize them. This is well documented especially in the case of β-glucuronidase and in the case of ribonuclease B (Arch. Biochem. Biophys. (1978) 188, 418; Advances in Enzymology, edited by A. Meister, New York (1974); Pediat. Res. (1977) 11, 816).

Taken as a whole, this information shows that the rapid elimination of immunotoxins can be explained by the recognition of the mannose residues of the A chain of ricin by the hepatic cells, in particular the Kupffer cells. The property of mannanes to inhibit the rapid plasma elimination of immunotoxins containing the A chain of ricin is also easily explained by the fact that the mannanes administered occupy the receptor cells of the glycoproteins and therefore oppose the recognition, by these receptors, of the polyosidic units carried by the A chain of ricin or by any conjugate containing the latter.

The property of mannanes to inhibit the rapid plasma elimination of immunotoxins containing the A chain of ricin is equally applicable, for the reasons indicated above, to the uncoupled A chain of ricin or to any natural, semi-synthetic or synthetic hybrid molecule containing the A chain of ricin, and in particular to any immunotoxins containing the A chain or ricin, irrespective of the type of bond chosen to join the antibody to the A chain of ricin. For the same reasons, this property of mannanes is more generally applicable to any immunotoxin, whatever the toxin used to produce it, provided this toxin or toxic sub-unit comprises polysaccharide groups containing mannose residues, in particular in the terminal position, regardless of the constituent antibody and regardless of the type of bond chosen to join the antibody to the toxin or toxic sub-unit.

The examples which follow provide a better understanding of the invention without limiting its scope.

EXAMPLE 1

The purpose of this example is to demonstrate the changes in elimination kinetics of immunotoxins (as well as their constituent components) in the presence or absence of mannane.

A—The following procedures were used:

(a) Measurement of the elimination kinetics of the immunotoxin IT-T101

The conjugate called IT-T101 is obtained by reacting an antibody directed against human T cells (antibody T101 directed against the antigen T65), substituted by an activated disulfide group, with the A chain of ricin. The preparation and cytotoxic properties of this conjugate were described in French Patent Application No. 8121836 in the name of the Applicant Company. The conjugate IT-T101 is administered to rabbits by a single injection into a vein in the ear. The quantity injected corresponds to 1.25 mg of immunotoxin per kg of body weight, i.e. 0.415 mg/kg expressed as A chain and 0.835 mg/kg expressed as antibody. Blood samples are taken at intervals on heparin. The plasma is analyzed by means of a radioimmunometric assay denoted hereafter by the abbreviation RIM-1.

This technique has the advantage of determining the immunotoxin without modifying it. This determination is carried out in microtitration plates (for example: "NUNC-TSP screening system", Poly Labo Block, France), the cover of which is provided with hyperabsorbent spikes dipping into the wells in the base. These spikes constitute the solid phases. Sheep antibodies directed against the A chain of ricin (denoted hereafter by the abbreviation Acl), purified by affinity chromatography, are adsorbed onto the solid phases. To do this, 200 μl of a solution of Acl containing 10 μg/ml in a buffer which is 20 mM in respect of phosphate, pH 7, and 150 mM in respect of NaCl are divided up into the wells. The spikes are brought into contact first with the solution of Acl for 24 hours at 4° C. and then with fetal calf serum for 3 hours at 20° C. in order to saturate all the fixation sites. The saturated immunoabsorbent is then brought into contact for 3 hours at 20° C. with the plasma samples at different dilutions, or with solutions of immunotoxin IT-T101 of known concentrations in order to establish the calibration curve. Washing is carried out with a buffer which is 20 mM in respect of phosphate, pH 7, and 150 mM in respect of NaCl, and the immunoabsorbent is then brought into contact for 2 hours at 20° C. with goat antibodies directed against mouse IgG, which have been purified by affinity chromatography and radiolabeled (denoted hereafter by the abbreviation Ac2). The Ac2 is radiolabeled with iodine 125 in the presence of chloramine T by the method of Greenwood and Hunter (Biochem. J., (1963) 89, 114); the specific activity of the radiolabeled Ac2 is 5 to 10 μCi/mg. $10^6$ cpm of radiolabeled Ac2 are introduced, in a volume of 200 ml, into a buffer which is 20 mM in respect of phosphate, pH 7, and 150 mM in respect of NaCl and contains 0.1% of bovine serum albumin. After washing in a buffer which is 20 mM in respect of phosphate, pH 7, and 150 mM in respect of NaCl, the spikes are detached and the quantity of bound Ac2 is measured by counting the radioactivity. The immunotoxin concentration in the samples to be determined is measured by reference to the calibration curve established with IT-T101 introduced at different known concentrations.

This test—by virtue of its principle of recognition—makes it possible to measure the intact immunotoxin molecules.

Furthermore, comparison of the concentrations obtained in this assay with those measured by the test for in vitro cytotoxic activity on target cells gives identical values, thereby ensuring that the immunotoxin determined by the RIM-1 test corresponds to molecules which have retained their property of cytotoxicity.

(b) Measurement of the elimination kinetics of the antibody directed against human T cells (or antibody T101)

This antibody was prepared and purified in the manner indicated in French Patent Application No. 8121836. The antibody T101 is injected intravenously into rabbits at a dose of 0.835 mg/kg. The plasma samples are taken as previously. The antibody concentration in the samples is measured by radioimmunometric assay (RIM-2). This assay is performed under the same conditions as the RIM-1 test, except that here the Ac1 solution is a solution containing 10 mg/ml of goat antibodies directed against mouse IgG, purified by affinity chromatography. The antibody Ac2 is identical to that in the RIM-1 test. The concentration of antibody T101 in the samples to be determined is measured by reference to the calibration curve established with the antibody T101 introduced at different known concentrations.

(c) Measurement of the elimination kinetics of the A chain of ricin

The A chain of ricin was prepared and purified in the manner indicated in French Patent No. 78/27838 and its Addition no. 79/24655 of the prior art. The A chain is injected intravenously into rabbits at a dose of 0.415 mg/kg. The plasma samples are taken as previously. The concentration of A chain in the samples is measured by radioimmunometric assay (RIM-3). This assay is performed under the same conditions as the RIM-1 test, the antibodies Ac1, absorbed on the solid phase, also being sheep antibodies directed against the A chain of ricin, purified by affinity chromatography, and the antibodies Ac2 being the same radiolabeled antibodies as described in RIM-1. The concentration of A chain of ricin in the samples to be determined is measured by reference to a calibration curve established with the A chain of ricin introduced at different known concentrations.

The values of the concentrations of immunotoxin, antibody and A chain of ricin in the plasma, measured by these three tests, are reproducible, reliable and quantitative. The detection threshold for these three products is 1 ng/ml. A study of the reproducibility within an assay and between assays gives variation coefficients below 10% for concentration values within the range from 1 to 200 ng/ml.

B—Results:

The results of the experiments carried out are represented in the form of curves showing, on the abscissa, the time expressed in hours and, on a logarithmic scale on the ordinate, the concentration of the product measured, expressed as a percentage of the theoretical plasma concentration at time zero. This value, called the "relative plasma concentration" (RPC), is calculated using the following expression:

$$RPC = \frac{\text{concentration measured at time } T}{\text{quantity injected/plasma volume}} \times 100$$

The plasma volume is considered to be equal to 36 ml/kg of body weight of the animal.

(a) In the absence of mannane: plasma elimination kinetics of the immunotoxin IT-T101, the antibody T101 and the A chain of ricin.

FIG. 1 shows the plasma elimination curve of IT-T101, which has two phases (curve 1). In the first phase, the product disappears rapidly (about 97% in 30 minutes); in the second phase, the decrease is slower. The first elimination phase observed with IT-T101 does not appear in the elimination kinetics of the antibody T101, where only one, slow elimination phase is recorded (curve 2). On the other hand, the plasma elimination kinetics of the uncoupled A chain are very comparable to those of IT-T101: 1 hour after injection, only 0.7% of the administered dose still remains in the plasma (curve 3).

(b) In the presence of mannane: plasma elimination kinetics of the immunotoxin IT-T101 and the A chain of ricin.

The mannane was administered according to the following scheme:

20% of the final dose of the polysacchardie is injected intravenously 10 minutes before the injection of IT-T101 or A chain. At time zero, 40% of the final dose of the polysaccharide is injected intravenously in association with IT-T101 or A chain (0.415 mg of A chain/kg). Then, 20% of the final dose of polysaccharide is injected intravenously at times 1.5 hours and 5 hours respectively.

FIG. 2 shows the plasma elimination curve, as a function of time, of IT-T101 injected intravenously in association with mannane at a total dose of 0.416 g/kg (curve 2). In the presence of mannane, the first elimination phase—responsible for the disappearance of the greater part of the product—is practically suppressed, leading to a major increase in the level of active immunotoxin in the plasma. 15 hours after injection, the concentration of IT-T101 is 100 times greater when the immunotoxin has been associated with mannane than when mannane is absent (curve 1).

This effect of inhibiting the elimination of the immunotoxin from the plasma depends on the dose of mannane. Lower doses of mannane (166 mg/kg and 16.6 mg/kg) produce weaker effects (curves 3 and 4).

Figure 3:
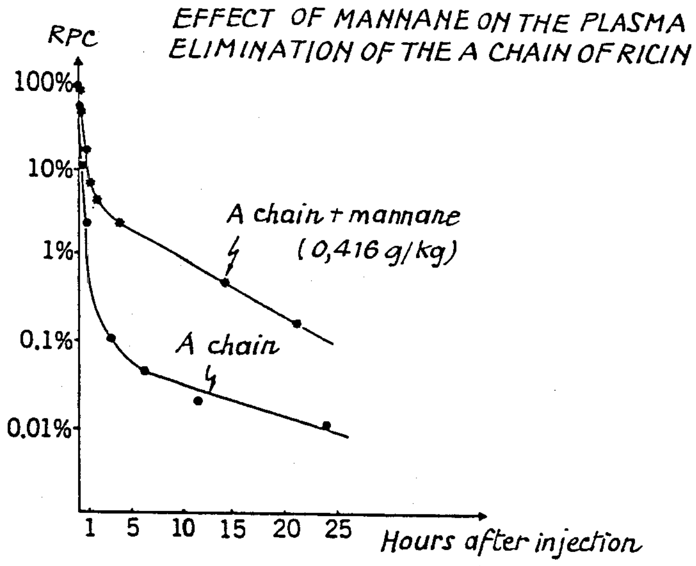

The properties of mannane are also observed with the uncoupled A chain, as shown in FIG. 3. This point confirms that the rapid disappearance of the immunotoxin is indeed attributable to the constituent A chain, in particular because of its terminal mannose residues.

It is seen nevertheless that the first elimination phase of the A chain is not totally suppressed, contrary to what happens with the immunotoxin. This confirms the totally surprising effect observed when mannane and immunotoxin are administered simultaneously.

EXAMPLE 2

To show a possible specificity of action of mannane, the plasma elimination kinetics of the immunotoxin IT-T101 were measured in the presence of other polysaccharides not possessing mannose residues in the terminal position, these polysaccharides being the dextrans T10, T40 or T500 (glucose polymers with respective molecular weights of about 10,000, 40,000 and 500,000) administered at a total dose of 416 mg/kg, galactan (galactose polymer) administered at a total dose of 166 mg/kg, and asialofetuine (highly glycosylated glycoprotein with terminal galactose) administered at a total dose of 166 mg/kg.

Figure 4:
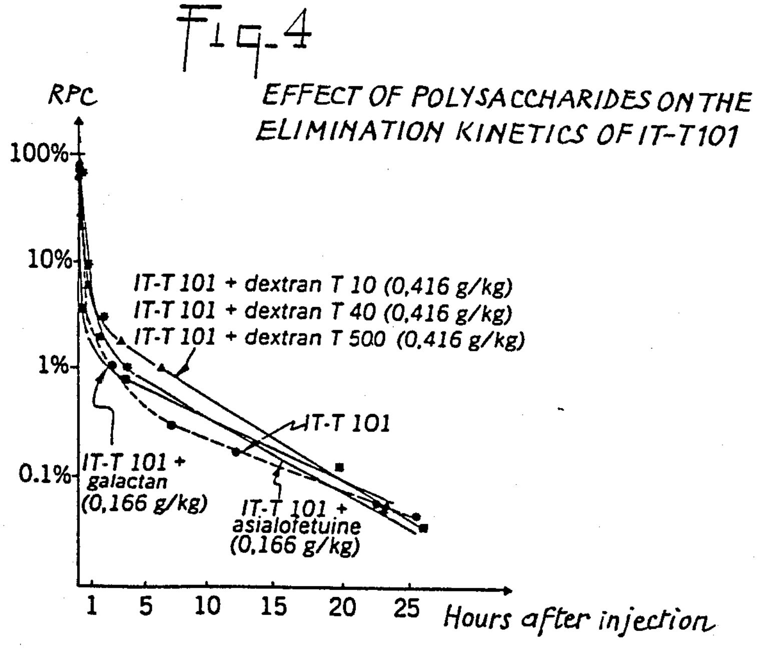

The curves illustrated in FIG. 4 show that these polysaccharides have virtually no effect on the plasma elimination kinetics of the immunotoxin IT-T101.

EXAMPLE 3

This example demonstrates the hepatic capture of the A chain of ricin after intravenous injection, and the inhibition of this capture by mannane.

Figure 5:
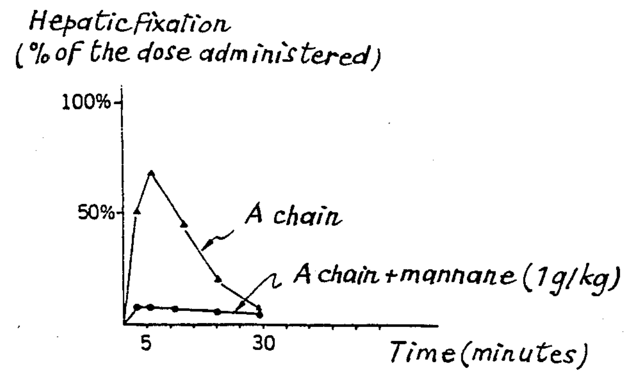

The A chain radiolabeled with iodine 125 is injected intravenously into Charles River France CD1 mice in the absence or presence of mannane at a dose of 1 g/kg. At different times during the experiment, two animals are anesthetized. The abdominal cavity is opened, the vena cava is cut and the liver is washed with 10 ml of physiological salt solution by injection into the portal vein. The liver is totally removed and the radioactivity is determined. The results are represented as a percentage of the number of cpm fixed to the liver, relative to the total number of cpm injected (FIG. 5). In the absence of mannane, the A chain of ricin is captured very quickly and efficiently by the liver, as indicated by the radioactivity peak. Conversely, in the presence of mannane, this radioactivity peak is practically suppressed. This result confirms that the A chain of ricin is trapped by the liver and that the maintenance of the immunotoxin, like the A chain, at high plasma levels in the presence of mannane is indeed due to the inhibition of this hepatic capture.

EXAMPLE 4

This example demonstrates the absence of an antagonistic effect of mannane towards the selective cytotoxicity of the immunotoxin IT-T101 in vitro.

In these experiments, the cytotoxicity was evaluated by measuring the incorporation of $^{14}C$-leucine by the target cells (CEM cells) after incubation for 24 hours at 38° C. in the presence of known concentrations of the immunotoxin studied, or of reference cytotoxic substances, in the absence or presence of mannane at a concentration of 10 mg/ml. The technique employed is the one described previously (J. Biol. Chem. 1984, 259 (15), 9359).

A check was carried out beforehand to show that mannane is not cytotoxic to the cells at the concentrations used. The results of these experiments are shown in Table I. The cytotoxic effect is measured by the value of the molar concentration ($IC_{50}$), expressed as A chain, which causes a 50% inhibition of the incorporation of the tracer.

The immunotoxin, by itself or in its form activated by ammonium chloride, fully retains its activity. In the same way, the intrinsic toxicity of the A chain is not modified. Thus, in the presence of mannane, the characteristic cytotoxic properties of the immunotoxin are not affected.

TABLE I

| Substances tested | $IC_{50}$ expressed as molarity of A chain: without mannane | with mannane (10 mg/ml) |
|---|---|---|
| Immunotoxin IT-T101 plus $NH_4Cl$ | $3.0 \cdot 10^{-13}$ M | $2.8 \cdot 10^{-13}$ M |
| IT-T101 | $1.0 \cdot 10^{-9}$ M | $1.2 \cdot 10^{-9}$ M |
| A chain | $7.0 \cdot 10^{-7}$ M | $7.0 \cdot 10^{-7}$ M |

EXAMPLE 5

Toxicity of the immunotoxin IT-T101 injected into mice in association with mannane.

It was important to check the overall toxicological effect of the association of immunotoxin plus mannane on the whole animal. This was done by determining the 50% lethal dose of the antimelanoma immunotoxin (IT-HM) administered intravenously to Charles River France CD1 mice in the absence of mannane or with the intravenous co-administration of 10 mg of mannane per mouse. The preparation and cytotoxic properties of this antimelanoma conjugate (IT-HM) were described in French Patent Application No. 81/07596.

The values found are indicated in Table II.

TABLE II

| Product tested | $LD_{50}$ |
|---|---|
| IT-HM by itself | 460 micrograms/mouse |
| IT-HM + 10 mg of mannane/mouse | 115 micrograms/mouse |

These results show a slight increase in toxicity of the immunotoxin when it is administered simultaneously with mannane. This increase in toxicity by a factor of only 4 does not restrict the in vivo use of mannane in view of the very significant effects in respect of maintaining the plasma concentration of immunotoxins in vivo, as demonstrated above.

EXAMPLE 6

The purpose of this example is to demonstrate the effect of mannane on the action of an immunotoxin in an "in vivo" experiment.

The experiment was carried out on BL 1.1 mice (negative Thy 1.2 cells) [International Journal of Cancer 24, 168–177, (1979)]. The immunotoxin used is the conjugate in which the antibody directed against Thy 1.2 (antibody AT15E) is associated by means of a disulfide bond with the A chain of ricin, and which is prepared by the process described in our Applications of the prior art.

The following protocol was used.

On day 0, groups of 10 BL 1.1 mice receive $5\times10^4$ T2 cells (positive Thy 1.2 cells of murine lymphoma) by intravenous injection and are randomized before treatment.

The treatment is carried out intravenously on day 1:

1 group receives 10 μg/mouse of the conjugate antibody AT15E/A chain of ricin by itself;

1 other group receives the same quantity of the same conjugate mixed with 10 mg of mannane.

In addition, 4 control groups respectively receive:

the culture medium RPMI (medium used for the culture of the T2 cells);

mannane by itself (10 mg/mouse);

the A chain of ricin (10 μg) and mannane (10 mg);

the A chain of ricin (10 μg), the antibody AT15E (30 μg) and mannane (10 mg).

The animals are observed for 50 days and the mortality is noted.

Figure 6:
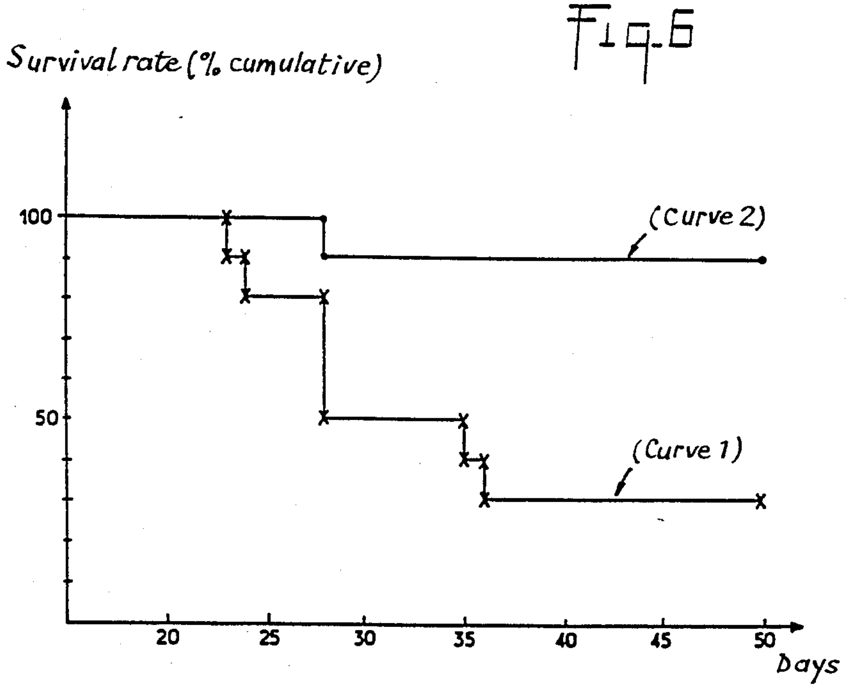

FIG. 6 shows the percentage of animals surviving as a function of the time which has elapsed since the treatment.

Curve 1 relates to the animals which received the immunotoxin by itself and curve 2 relates to the animals which received the combination of immunotoxin plus mannane.

As can be seen, the immunotoxin/mannane association gave a survival rate of 90% fifty days after the treatment, whereas the administration of the immunotoxin by itself gave an animal survival rate of only 30% after 50 days.

Furthermore, the following observations were made on day 50 for the control groups (not shown on FIG. 6):

0% survival rate for the animals treated with RPMI and with A chain plus mannane;

10% survival rate for the animals receiving mannane by itself;

20% survival rate for the animals treated with A chain of ricin+antibody+mannane.

These results show the efficacy of the immunotoxin/-mannane combination compared with the immunotoxin used by itself and compared with the control substances.

The combination consisting of an immunotoxin and mannane can therefore be used as a drug in human therapy. This combination can be used for the treatment of cancerous or non-cancerous complaints in which the target cells will be recognized by the antibody used to prepare the immunotoxin.

With the aim of eliminating all the target cells, the treatment must be carried out with a sufficient dose of immunotoxin associated with a quantity of mannane which can vary from 10 mg to 1 g/kg for each administration of immunotoxin. The optimum modalities for administration of the constituents of the combination, and also the duration of the treatment, will have to be determined in each case according to the subject and the nature of the complaint to be treated.

The new drugs accordingg to the invention are packaged for administration by injection, preferably intravenous injection. The constituents of the combination will preferably be stored separately and may be mixed as required, for immediate use, in the syringe or the perfusion solvent.

What is claimed is:

1. A pharmaceutical composition comprising a combination of at least one immunotoxin and at least one mannose-containing polymer.

2. A pharmaceutical composition as claimed in claim 1, wherein the immunotoxin comprises a natural, semisynthetic or synthetic toxin, toxic sub-unit or fragment of a toxic sub-unit comprising polysaccharide groups containing mannose residues and an antibody component; and the mannose-containing polymer is a polyoside or polysaccharide carbohydrate polymer which has an average molecular weight greater than 1000 and contains a large portion of mannose residues.

3. A pharmaceutical composition as claimed in claim 1 wherein the immunotoxin is anti-T65 coupled to the A-chain of ricin and the mannose-containing polymer is a mannan.

4. A pharmaceutical composition according to claim 2 packaged for administration by injection.

5. A pharmaceutical composition as claimed in claim 2 wherein the mannose-containing polymer contains from 20–100% of mannose residues.

6. A method to inhibit the rapid plasma elimination of immunotoxins comprising a natural, semisynthetic or synthetic toxin, toxic sub-unit or fragment of a toxic sub-unit comprising polysaccharide groups containing mannose residues joined to an antibody component which comprises providing an effective amount for inhibiting the elimination of the immunotoxin from the plasma of at least one mannose-containing polymer.

7. A method as claimed in claim 6 wherein the mannose-containing polymer is mannan.

8. A method as claimed in claim 6 wherein the effective amount of at least one mannose-containing polymer is from 10 mg to 1 g/kg for each administration of immunotoxin.

9. A kit for the preparation of a pharmaceutical composition comprising a combination of at least one immunotoxin and at least one mannose-containing polymer, and wherein the immunotoxin and the mannose-containing polymer are packaged separately within the kit and at least a portion of the immunotoxin and the mannose-containing polymer are mixed prior to use.

10. A kit as claimed in claim 9 wherein the immunotoxin is anti-T65 coupled to the A chain of ricin and the mannose-containing polymer is mannan.

* * * * *